United States Patent [19]

Teach

[11] Patent Number: 4,483,706
[45] Date of Patent: Nov. 20, 1984

[54] HALOACYL AND THIOHALOACYL ARYL-SUBSTITUTED OXAZOLIDINES AND THIAZOLIDINES HERBICIDAL ANTIDOTES

[75] Inventor: Eugene G. Teach, El Cerrito, Calif.

[73] Assignee: Stauffer Chemical Company, Westport, Conn.

[21] Appl. No.: 492,271

[22] Filed: May 6, 1983

Related U.S. Application Data

[60] Division of Ser. No. 317,957, Nov. 4, 1981, , which is a division of Ser. No. 840,973, Oct. 11, 1977, Pat. No. 4,322,240, which is a division of Ser. No. 627,986, Nov. 3, 1975, Pat. No. 4,072,688, which is a continuation-in-part of Ser. No. 550,069, Feb. 14, 1975, abandoned.

[51] Int. Cl.$^3$ ..................... A01N 43/76; A01N 43/78
[52] U.S. Cl. ........................................... 71/88; 71/90
[58] Field of Search ..................................... 71/88, 90

[56] References Cited

U.S. PATENT DOCUMENTS

| | | |
|---|---|---|
| 3,311,655 | 3/1967 | Boileau et al. ............... 260/471 |
| 3,546,231 | 12/1970 | King et al. ................ 260/294.8 |
| 3,884,671 | 5/1975 | Albright et al. ................. 71/88 |
| 3,945,998 | 3/1976 | Anderson et al. ............ 260/240 |
| 3,989,503 | 11/1976 | Pallos et al. .................... 71/88 |
| 4,021,224 | 5/1977 | Pallos et al. .................... 71/88 |
| 4,044,018 | 8/1977 | Tomita et al. ................ 260/307 |
| 4,071,349 | 1/1978 | Arneklev et al. ............... 71/88 |

OTHER PUBLICATIONS

Sunagawa et al., "Reaction of Schiff Bases, etc.", Yakugaku Zasshi 82. 826-833 CA 58:5649-51.

*Primary Examiner*—Robert Gerstl
*Attorney, Agent, or Firm*—Harry A. Pacini

[57] ABSTRACT

Haloacyl and thiohaloacyl aryl-substituted oxazolidines and thiazolidines useful as active antidotes against crop injury when used with various herbicides; herbicidal compositions and utility of various herbicides and aryl substituted oxazolidines and thiazolidines having the formula

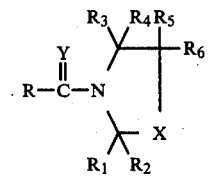

wherein X and Y are independently oxygen or sulfur; R is haloalkyl or chloroalkenyl; $R_1$ is hydrogen, lower alkyl, phenyl, naphthyl, substituted phenyl wherein said substituents are monofluoro, mono- or di- chloro, nitro, methyl, methoxy, or hydroxy; $R_2$ is hydrogen or lower alkyl; $R_3$ is hydrogen, lower alkyl, hydroxymethyl, N-methyl carbamoyloxymethyl or dichloroacetoxymethyl; $R_4$ is hydrogen or lower alkyl; $R_5$ is hydrogen, lower alkyl or phenyl; and $R_6$ is hydrogen; provided that at least one of $R_1$ or $R_5$ is phenyl, substituted phenyl or naphthyl.

47 Claims, No Drawings

HALOACYL AND THIOHALOACYL ARYL-SUBSTITUTED OXAZOLIDINES AND THIAZOLIDINES HERBICIDAL ANTIDOTES

CROSS-REFERENCE TO PRIOR APPLICATION

This is a division of application Ser. No. 317,957, filed Nov. 4, 1981 which in turn is a divisional of U.S. Ser. No. 840,973, filed Oct. 11, 1977, now U.S. Pat. No. 4,322,240, issued Mar. 30, 1982, which in turn is a divisional of U.S. Ser. No. 627,986, filed Nov. 3, 1975, now U.S. Pat. No. 4,072,688, issued Feb. 7, 1978, which in turn is a continuation-in-part of U.S. Ser. No. 550,069, filed Feb. 14, 1975, now abandoned.

BACKGROUND OF THE INVENTION

While many herbicides are immediately toxic to a large number of weed pests, it is known that the effect of many herbicides upon important plant cultivations is either non-selective or not adequately selective. Thus, many herbicides damage not only the weeds to be controlled but, to a greater or lesser extent, the desirable cultivated plants as well. This holds true for many herbicidal compounds which have been commercially successful and are commercially available. These herbicides include types such as triazines, urea derivatives, halogenated acetanilides, carbamates, thiocarbamates and the like. Some examples of these compounds are described in U.S. Pat. Nos. 2,913,327, 3,037,853, 3,175,897, 3,185,720, 3,198,786 and 3,582,314.

The side effect of injury to a cultivated crop by various herbicides is particularly inconvenient and unfortunate. When used in the recommended amounts in the soil to control broadleaf weeds and grasses, serious malformation or stunting of the crop plants sometimes result. This abnormal growth in the crop plants results in loss of crop yield. The search continues for good selective herbicides.

Previous attempts are described to overcome this problem. The treatment of the crop seed with certain "hormonal" antagonistic agents prior to planting is described; see U.S. Pat. Nos. 3,131,509 and 3,564,768. The protective agents, as well as the herbicide, in these prior processes are largely specific to certain cultivated plant species. The antagonistic agents have not been notably successful. The aforementioned patents specifically exemplify and describe the treatment of seeds employing compounds of a different chemical class, not suggestive of the present invention.

DESCRIPTION OF THE INVENTION

It has been discovered that cultivated crop plants can be protected against injury by thiocarbamate-type herbicides and by halogenated acetanilide herbicides, each alone or in mixtures or combination with other compounds. Further, as an alternative effect, the tolerance of the plants to these herbicides can be substantially increased by adding to the soil an antidote compound corresponding to the following formula

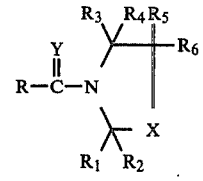

wherein X and Y are independently oxygen or sulfur; R is halo-alkyl or chloro alkenyl; $R_1$ is hydrogen, lower alkyl, phenyl, naphthyl, substituted phenyl wherein said substituents are mono-fluoro, mono- or di- chloro, nitro, methyl, methoxy or hydroxyl; $R_2$ is hydrogen or lower alkyl; $R_3$ is hydrogen or lower alkyl; $R_4$ is hydrogen, lower alkyl, hydroxymethyl, N-methyl carbamoyloxymethyl or dichloroacetoxymethyl; $R_5$ is hydrogen, lower alkyl or phenyl; and $R_6$ is hydrogen; provided that at least one of $R_1$ or $R_5$ is phenyl, substituted phenyl or naphthyl.

Certain of the compounds disclosed herein are considered new compositions and correspond to the following formula

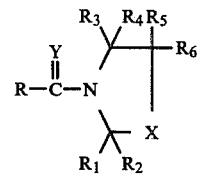

in which X and Y are independently oxygen or sulfur; R is halo-alkyl or chloroalkenyl; $R_1$ is hydrogen, lower alkyl or phenyl; $R_2$ is hydrogen or lower alkyl; $R_3$ is hydrogen or lower alkyl; $R_4$ is hydrogen or lower alkyl; $R_5$ is phenyl and $R_6$ is hydrogen.

In the above description, the following embodiments are intended for the various substituent groups: For R, halo-alkyl preferably includes those members which contain from 1 to 6 carbon atoms, inclusive, in both straight chain and branched chain configurations and the term halo includes chloro and bromo as mono, di, tri and tetra substitutions. As exemplary of the alkyl portion within the preferred embodiment are the following: Methyl, ethyl, n-propyl, isopropyl, n-butyl, sec.-butyl, 1,1-dimethylbutyl, amyl, isoamyl, n-hexyl and isohexyl. For R, chloro alkenyl preferably includes those members which contain from 2 to 4 carbon atoms and at least one olefinic double bond and the chloro substituents are present as mono-, di-, tri-, or tetra- substitutions, such as trichlorovinyl. For $R_1$, $R_2$, $R_3$, $R_4$ and $R_5$, lower alkyl in each instance preferably includes those members which contain from 1 to 4 carbon atoms, inclusive, in both straight chain and branched chain configurations, for example, methyl, ethyl, n-propyl, isopropyl, n-butyl, sec.-butyl, tert.-butyl and the like.

As an alternative mode of action, the compounds of this invention may interfere with the normal herbicidal action of the thiocarbamate-type and other herbicides to render them selective in their action. Whichever mode of action is present, the corresponding beneficial and desirable effect is the continued herbicidal effect of the thiocarbamate with the accompanying decreased herbicidal effect on desired crop species. This advantage and utility will become more apparent hereinafter.

Therefore, the terms herbicide antidote or antidotal amount, is meant to describe that effect which tends to counteract the normal injurious herbicidal response that the herbicide might otherwise produce. Whether it is to be termed a remedy, interferant, protectant, or the like, will depend upon the exact mode of action. The mode of action is varied, but the effect, which is desirable, is the result of the method of treating the soild in which a crop is planted. Hitherto, there have been no systems which have been satisfactory for this purpose.

The compounds of this invention represented by the above formula can be prepared by several different procedures depending upon the starting materials.

The oxazolidine and thiazolidine intermediates were prepared by the condensation of the amino alcohol or mercaptan with a suitable aldehyde or ketone in boiling benzene with the continuous separation of water. This method is described by Bergmann et al., JACS 75 358 (1953). Usually, the oxazolidines and thiazolidines intermediates were pure enough to be used directly without further purification. Aliquots of these solutions were then used to prepare the compounds of this invention.

Compounds having a 3-thioacyl substitution may be prepared from the corresponding oxygen analogues by methods known in the synthetic organic literature, such as treatment with $P_2S_5$ in benzene at reflux.

The appropriate intermediate was reacted with an acid chloride in the presence of a hydrogen chloride acceptor, such as triethylamine, to prepare the desired compound. Work-up and purification procedures involved standard methods of extraction, distillation or crystallization.

The compounds of the present invention and their preparation are more particularly illustrated by the following examples. Following the examples of preparation is a table of compounds which are prepared according to the procedures described herein. Compound numbers have been assigned to them and are used for identification throughout the balance of the specification.

EXAMPLE I

Preparation of 2-m-nitrophenyl-3-dichloroacetyl oxazolidine

Five and eight tenths (5.8) grams of 2-m-nitrophenyl oxazolidine was dissolved in 50 ml. methylene chloride containing 3.5 g. of triethylamine. Dichloroacetyl chloride 4.4 g. was added dropwise with stirring to the reaction flask and cooled in a water bath at room temperature. When addition was complete, the mixture was stirred at room temperature for about 30 minutes, washed with water, separated and dried over anhydrous magnesium sulfate. The solvent was stripped off under vacuum. There was obtained a yield of 8.6 g. of the title compound, $N_D^{30} = 1.5590$.

EXAMPLE II

Preparation of 2-ethyl-3-dichloroacetyl-5-phenyl oxazolidine

Twenty-one and three tenths (21.3) ml. of a solution containing 5.3 g. of 2-ethyl-5-phenyl oxazolidine was diluted with 25 ml. of benzene and 3.1 g. of triethylamine was added. The mixture was cooled in a room temperature water bath and 4.4 g. of dichloroacetyl chloride was added dropwise with stirring. The stirring was continued for about 30 minutes after addition was complete. The solution was washed with water, separated, dried over magnesium sulfate and removed under vacuum. There was obtained a yield of 8.7 g. of the title compound, an oil, $N_D^{30} = 1.5600$.

EXAMPLE III

Preparation of 2,2-dimethyl-3-dichloroacetyl-5-phenyl oxazolidine

One hundred (100) grams of 1-phenyl-2-amino ethanol was dissolved in 250 ml. of benzene and 45 g. of acetone was added. The mixture was heated at reflux for several hours while about 15 ml. of water was removed with a modified Dean-Stark apparatus. The mixture was cooled and 75 ml. of triethylamine was added, followed by 108 g. of dichloroacetyl chloride added dropwise with stirring and cooling in a room temperature water bath. The solution was allowed to stand after addition was complete, washed with water, dried over anhydrous magnesium sulfate, and the solvent stripped under vacuum. The thick oil wt. 170 g. crystallized on standing and was triturated with dry ether to give 132 g. of the title compound, a white solid, m.p. 99.5°–100.5° C.

EXAMPLE IV

Preparation of 2-α-naphthyl-3-chloroacetyl oxazolidine

Nineteen and nine tenths (19.9) ml of a benzene solution containing 5 g. of 2-α-naphthyl oxazolidine was combined with 50 ml. of benzene and 2.8 g. of chloroacetyl chloride. To this was added 2.6 g. of triethylamine, dropwise with stirring in an ice bath. The mixture was stirred at room temperature for 30 minutes after addition was complete, washed with water, separated and dried over magnesium sulfate. The solvent was stripped under vacuum. There was obtained a yield of 6.7 g. of an oil, the title compound, $N_D^{30} = 1.6030$.

EXAMPLE V

Preparation of 2-phenyl-3-chloroacetyl-4,4-dimethyl oxazolidine

Twenty-one and three tenths (21.3) ml. of a benzene solution containing 5.3 g. of 2-phenyl-4,4-dimethyl oxazolidine was mixed with 50 ml. of benzene and 3.4 g. of chloroacetyl chloride. To this solution was added 3.1 g. of triethylamine, dropwise with stirring in an ice bath. The mixture was stirred for about 30 minutes after addition was complete and then washed with water, separated and dried over magnesium sulfate and the solvent stripped. There was obtained a yield of 6.5 g. of an oil, the title compound, $N_D^{30} = 1.5364$.

EXAMPLE VI

Preparation of 2-phenyl-3-dichloroacetyl thiazolidine

Five (5) grams of 2-phenyl thiazolidine was dissolved in 50 ml. of acetone, 3.1 g. of thiethylamine was added and the mixture stirred in a room temperature water bath, while 4.4 g. of dichloroacetyl chloride was added dropwise. The mixture was allowed to stand for about 30 minutes and then poured into water, extracted with methylene chloride, separated, dried over magnesium sulfate, and the solvent stripped under vacuum. There was obtained a yield of 7.3 g. of an oil, the title compound, $N_D^{30} = 1.5836$.

EXAMPLE VII

Preparation of 2-m-chlorophenyl-3-dichloroacetyl thiazolidine

Five (5) grams of 2-m-chlorophenyl thiazolidine was dissolved in 50 ml. of benzene and 2.6 g. of triethylamine and the mixture was stirred in a room temperature water bath, while 3.7 g. of dichloroacetyl chloride was added dropwise. After standing for about 30 minutes, the mixture was washed with water, separated and dried over magnesium sulfate and the benzene stripped under vacuum. There was obtained a yield of 7.2 g. of an oil, the title compound, $N_D^{30} = 1.5805$.

EXAMPLE VIII

Preparation of 2(2',6'-dichlorophenyl)3-chloroacetyl thiazolidine

Twenty-three and five tenths (23.5) ml. of a benzene solution containing 5.9 g. of 2(2',6'-dichlorophenyl) thiazolidine was combined with 25 ml. of benzene and 2.8 g. of chloroacetyl chloride and the mixture stirred in an ice bath, while 2.6 g. of triethylamine was added dropwise. After standing for about 30 minutes the mixture was washed with water, separated, dried over magnesium sulfate and the benzene stripped off under vacuum. There was obtained a yield of 8 g. of an oil, the title compound, $N_D^{30} = 1.6041$.

EXAMPLE IX

Preparation of 3(3-bromopropionyl)5-phenyl oxazolidine

Four and five tenths (4.5) grams of 5-phenyl oxazolidine contained in 44.7 g. of benzene solution was mixed with 3.1 g. of triethylamine and stirred in a room temperature water bath, while 5.2 g. of 3-bromopropionyl chloride was added dropwise. After standing for about 30 minutes, the solution was washed with water, separated, dried over magnesium sulfate and the solvent stripped under vacuum. There was obtained a yield of 6 g. of an oil, the title compound, $N_D^{30} = 1.5591$.

EXAMPLE X

Preparation of 2,2,4-trimethyl-3-dichloroacetyl-5-phenyl oxazolidine

Twenty-three (23) ml. of a benzene solution containing 5.7 g. of 2,2,4-trimethyl-5-phenyl oxazolidine was mixed with 25 ml. of benzene and 3.1 g. of triethylamine and stripped at room temperature, while 4.4 g. of dichloroacetyl chloride was added dropwise. After standing for about 30 minutes, the mixture was washed with water, separated, dried over magnesium sulfate and stripped under vacuum. The product which crystallized was extracted with ether and precipitated with pentane. There was obtained 3.9 g. of a solid, the title compound, m.p. 126° C.

EXAMPLE XI

Preparation of 2-p-chlorophenyl-3-dichloroacetyl oxazolidine

Twenty-two (22) ml. of a benzene solution containing 5.5 g. of 2-p-chlorophenyl oxazolidine was mixed with 25 ml. of benzene and 3.1 g. of triethylamine and stirred at room temperature, while 4.4 g. of dichloroacetyl chloride was added dropwise. The mixture was allowed to stand for about 30 minutes, washed with water, separated, dried over magnesium sulfate and then stripped. There was obtained a yield of 8.4 g. of an oil, the title compound, $N_D^{30} = 1.5668$.

EXAMPLE XII

Preparation of 2,5-diphenyl-3(2,3-dibromopropionyl) oxazolidine

Four and five tenths (4.5) grams of 2,5-diphenyl oxazolidine was dissolved in 50 ml. of methylene chloride and 5 g. of 2,3-dibromopropionyl chloride was added and the mixture stirred in an ice bath, while 2.1 g. of triethylamine was added dropwise. After standing for about 30 minutes, the mixture was washed with water, separated and dried over magnesium sulfate and stripped under vacuum. There was obtained a yield of 7.1 g. of an oil, the title compound, $N_D^{30} = 1.5734$.

The following is a table of the compounds which are prepared according to the aforementioned procedures. Compound numbers have been assigned to them and are used for identification throughout the balance of the specification.

TABLE I

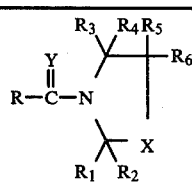

| COMPOUND NUMBER | R | $R_1$ | $R_2$ | $R_3$ | $R_4$ | $R_5$ | $R_6$ | X | Y | M.P. or $N_D^{30}$ |
|---|---|---|---|---|---|---|---|---|---|---|
| 1 | $CHCl_2$ | $m-NO_2-C_6H_4$ | H | H | H | H | H | O | O | 1.5590 |
| 2 | $CHCl_2$ | $m-NO_2-C_6H_4$ | H | $CH_3$ | $CH_3$ | H | H | O | O | 1.5448 |
| 3 | $CH_2Cl$ | $m-NO_2-C_6H_4$ | H | $CH_3$ | $CH_3$ | H | H | O | O | 1.5484 |
| 4 | $CHCl_2$ | $C_6H_5$ | H | H | H | H | H | O | O | 1.5490 |
| 5 | $CCl_3$ | $C_6H_5$ | H | H | H | H | H | O | O | 1.5398 |
| 6 | $CHBrCH_3$ | $C_6H_5$ | H | H | H | H | H | O | O | 1.5490 |
| 7 | $CCl_2-CH_3$ | $C_6H_5$ | H | H | H | H | H | O | O | 1.5301 |
| 8 | $CHBr_2$ | $C_6H_5$ | H | H | H | H | H | O | O | 1.5808 |
| 9 | $CHBrCH_2Br$ | $C_6H_5$ | H | H | H | H | H | O | O | 1.5712 |
| 10 | $CCl=CCl_2$ | $C_6H_5$ | H | H | H | H | H | O | O | 1.5615 |
| 11 | $CHCl_2$ | $m-ClC_6H_4$ | H | H | H | H | H | O | O | 1.5550 |
| 12 | $CCl_3$ | $m-ClC_6H_4$ | H | H | H | H | H | O | O | 1.5475 |

TABLE I-continued $$R-\overset{\overset{Y}{\|}}{C}-N\underset{R_1\ R_2}{\overset{R_3}{<}}\underset{}{\overset{R_4\ R_5}{C}-\underset{X}{C}-R_6}$$

| COMPOUND NUMBER | R | $R_1$ | $R_2$ | $R_3$ | $R_4$ | $R_5$ | $R_6$ | X | Y | M.P. or $N_D^{30}$ |
|---|---|---|---|---|---|---|---|---|---|---|
| 13 | CH$_2$Cl | m-ClC$_6$H$_4$ | H | H | H | H | H | O | O | 1.5590 |
| 14 | CH$_2$Br | m-ClC$_6$H$_4$ | H | H | H | H | H | O | O | 1.5720 |
| 15 | CHBrCH$_3$ | m-ClC$_6$H$_4$ | H | H | H | H | H | O | O | 1.5590 |
| 16 | CHBr$_2$ | m-ClC$_6$H$_4$ | H | H | H | H | H | O | O | 1.5833 |
| 17 | CHBrCH$_2$Br | m-ClC$_6$H$_4$ | H | H | H | H | H | O | O | 1.5718 |
| 18 | CHCl$_2$ | C$_6$H$_5$ | H | C$_2$H$_5$ | H | H | H | O | O | 1.5353 |
| 19 | CCl$_3$ | C$_6$H$_5$ | H | C$_2$H$_5$ | H | H | H | O | O | 1.5310 |
| 20 | CHCl$_2$ | C$_2$H$_5$ | H | H | H | C$_6$H$_5$ | H | O | O | 1.5600 |
| 21 | CCl$_3$ | C$_2$H$_5$ | H | H | H | C$_6$H$_5$ | H | O | O | 1.5455 |
| 22 | CHCl$_2$ | CH$_3$ | CH$_3$ | H | H | C$_6$H$_5$ | H | O | O | 1.5438 |
| 23 | CH$_2$Cl | CH$_3$ | CH$_3$ | H | H | C$_6$H$_5$ | H | O | O | 1.5450 |
| 24 | CHCl$_2$ | p-CH$_3$—C$_6$H$_4$ | H | H | H | H | H | O | O | 1.5440 |
| 25 | CCl$_3$ | p-CH$_3$—C$_6$H$_4$ | H | H | H | H | H | O | O | 1.5430 |
| 26 | CHBrCH$_2$Br | p-CH$_3$—C$_6$H$_4$ | H | H | H | H | H | O | O | 1.5627 |
| 27 | CCl$_2$CH$_3$ | p-CH$_3$—C$_6$H$_4$ | H | H | H | H | H | O | O | 1.5370 |
| 28 | CH$_2$Cl | p-CH$_3$—C$_6$H$_4$ | H | H | H | H | H | O | O | 1.5600 |
| 29 | CH$_2$Cl | m-CH$_3$O—C$_6$H$_4$ | H | H | H | H | H | O | O | 1.5570 |
| 30 | CHCl$_2$ | m-CH$_3$O—C$_6$H$_4$ | H | H | H | H | H | O | O | 1.5557 |
| 31 | CCl$_3$ | m-CH$_3$O—C$_6$H$_4$ | H | H | H | H | H | O | O | 1.5479 |
| 32 | CCl$_2$CH$_3$ | m-CH$_3$O—C$_6$H$_4$ | H | H | H | H | H | O | O | 1.5380 |
| 33 | CHBrCH$_2$Br | m-CH$_3$O—C$_6$H$_4$ | H | H | H | H | H | O | O | 1.5688 |
| 34 | CH$_2$Cl | 1-naphthyl | H | H | H | H | H | O | O | 1.6030 |
| 35 | CHCl$_2$ | 1-naphthyl | H | H | H | H | H | O | O | 1.5980 |
| 36 | CCl$_3$ | 1-naphthyl | H | H | H | H | H | O | O | 1.5132 |
| 37 | CCl$_2$CH$_3$ | 1-naphthyl | H | H | H | H | H | O | O | 1.5921 |
| 38 | CH$_2$Cl | C$_6$H$_5$ | H | H | H | CH$_3$ | H | O | O | 1.5486 |
| 39 | CHCl$_2$ | C$_6$H$_5$ | H | H | H | CH$_3$ | H | O | O | 1.5423 |
| 40 | CCl$_3$ | C$_6$H$_5$ | H | H | H | CH$_3$ | H | O | O | 1.5376 |
| 41 | CCl$_2$CH$_3$ | C$_6$H$_5$ | H | H | H | CH$_3$ | H | O | O | 1.5530 |
| 42 | CH$_2$Cl | C$_6$H$_5$ | H | CH$_3$ | CH$_3$ | CH$_3$ | H | O | O | 1.5364 |
| 43 | CHCl$_2$ | C$_6$H$_5$ | H | CH$_3$ | CH$_3$ | CH$_3$ | H | O | O | 1.5343 |
| 44 | CCl$_3$ | C$_6$H$_5$ | H | CH$_3$ | CH$_3$ | CH$_3$ | H | O | O | 1.5310 |
| 45 | CCl$_2$CH$_3$ | C$_6$H$_5$ | H | CH$_3$ | CH$_3$ | CH$_3$ | H | O | O | 1.5213 |
| 46 | CH$_2$Cl | C$_6$H$_5$ | H | H | H | H | H | S | O | 1.5804 |
| 47 | CHCl$_2$ | C$_6$H$_5$ | H | H | H | H | H | S | O | 1.5836 |
| 48 | CCl$_3$ | C$_6$H$_5$ | H | H | H | H | H | S | O | 1.5950 |
| 49 | CCl$_2$CH$_3$ | C$_6$H$_5$ | H | H | H | H | H | S | O | 1.5798 |
| 50 | CH$_2$CH$_2$Br | C$_6$H$_5$ | H | H | H | H | H | S | O | 1.5983 |
| 51 | CHBrCH$_2$Br | C$_6$H$_5$ | H | H | H | H | H | S | O | 110–112 |
| 52 | CH$_2$Cl | m-ClC$_6$H$_4$ | H | H | H | H | H | S | O | 1.5925 |
| 53 | CHCl$_2$ | m-ClC$_6$H$_4$ | H | H | H | H | H | S | O | 1.5805 |
| 54 | CCl$_3$ | m-ClC$_6$H$_4$ | H | H | H | H | H | S | O | 1.5940 |
| 55 | CCl$_2$CH$_3$ | m-ClC$_6$H$_4$ | H | H | H | H | H | S | O | 1.5850 |
| 56 | CH$_2$CH$_2$Br | m-ClC$_6$H$_4$ | H | H | H | H | H | S | O | 1.5931 |
| 57 | CHBrCH$_2$Br | m-ClC$_6$H$_4$ | H | H | H | H | H | S | O | 1.6038 |
| 58 | CH$_2$CH$_2$Cl | m-ClC$_6$H$_4$ | H | H | H | H | H | S | O | 1.5920 |
| 59 | CH$_2$Cl | 3,5-Cl$_2$—C$_6$H$_3$ | H | H | H | H | H | O | O | 1.5748 |

TABLE I-continued

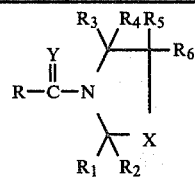

| COMPOUND NUMBER | R | $R_1$ | $R_2$ | $R_3$ | $R_4$ | $R_5$ | $R_6$ | X | Y | M.P. or $N_D^{30}$ |
|---|---|---|---|---|---|---|---|---|---|---|
| 60 | $CHCl_2$ | $3,5\text{-}Cl_2\text{—}C_6H_3$ | H | H | H | H | H | O | O | 1.5663 |
| 61 | $CCl_3$ | $3,5\text{-}Cl_2\text{—}C_6H_3$ | H | H | H | H | H | O | O | 1.5613 |
| 62 | $CCl_2CH_3$ | $3,5\text{-}Cl_2\text{—}C_6H_3$ | H | H | H | H | H | O | O | 1.5530 |
| 63 | $CH_2Cl$ | $3,5\text{-}Cl_2\text{—}C_6H_3$ | H | H | H | H | H | S | O | 1.6041 |
| 64 | $CHCl_2$ | $3,5\text{-}Cl_2\text{—}C_6H_3$ | H | H | H | H | H | S | O | 1.6038 |
| 65 | $CCl_3$ | $3,5\text{-}Cl_2\text{—}C_6H_3$ | H | H | H | H | H | S | O | 1.5962 |
| 66 | $CCl_2CH_3$ | $3,5\text{-}Cl_2\text{—}C_6H_3$ | H | H | H | H | H | S | O | 1.5908 |
| 67 | $CH_2Cl$ | H | H | H | H | $C_6H_5$ | H | O | O | 1.5640 |
| 68 | $CHCl_2$ | H | H | H | H | $C_6H_5$ | H | O | O | 1.5593 |
| 69 | $CCl_3$ | H | H | H | H | $C_6H_5$ | H | O | O | 1.5558 |
| 70 | $CHBr\text{—}CH_2Br$ | H | H | H | H | $C_6H_5$ | H | O | O | 1.5738 |
| 71 | $CCl_2CH_3$ | H | H | H | H | $C_6H_5$ | H | O | O | 1.5433 |
| 72 | $CH_2\text{—}CH_2Br$ | H | H | H | H | $C_6H_5$ | H | O | O | 1.5591 |
| 73 | $CHCl_2$ | $m\text{-}OH\text{—}C_6H_4$ | H | H | H | H | H | O | O | Waxy Solid |
| 74 | $CCl_2CH_3$ | $m\text{-}OH\text{—}C_6H_4$ | H | H | H | H | H | O | O | 1.5453 |
| 75 | $CHCl_2$ | $p\text{-}NO_2\text{—}C_6H_4$ | H | H | H | H | H | S | O | 1.6008 |
| 76 | $CHCl_2$ | $C_6H_5$ | H | $C_2H_5$ | H | H | H | S | O | 1.5352 |
| 77 | $CHCl_2$ | $C_6H_5$ | H | $CH_3$ | $CH_3$ | H | H | S | O | 1.5366 |
| 78 | $CH_2Cl$ | $CH_3$ | $CH_3$ | $CH_3$ | H | $C_6H_5$ | H | O | O | 1.5021 |
| 79 | $CHCl_2$ | $CH_3$ | $CH_3$ | $CH_3$ | H | $C_6H_5$ | H | O | O | 126° C. |
| 80 | $CCl_3$ | $CH_3$ | $CH_3$ | $CH_3$ | H | $C_6H_5$ | H | O | O | 1.5080 |
| 81 | $CH_2BrCH_2$ | $CH_3$ | $CH_3$ | $CH_3$ | H | $C_6H_5$ | H | O | O | 1.5051 |
| 82 | $CH_2BrCHBr$ | $CH_3$ | $CH_3$ | $CH_3$ | H | $C_6H_5$ | H | O | O | 1.5450 |
| 83 | $CH_2Cl$ | $o\text{-}Cl\text{—}C_6H_4$ | H | H | H | H | H | O | O | 1.5578 |
| 84 | $CHCl_2$ | $o\text{-}Cl\text{—}C_6H_4$ | H | H | H | H | H | O | O | 1.5595 |
| 85 | $CH_2BrCHBr$ | $o\text{-}Cl\text{—}C_6H_4$ | H | H | H | H | H | O | O | 1.5794 |
| 86 | $CH_2Cl$ | $p\text{-}Cl\text{—}C_6H_4$ | H | H | H | H | H | O | O | 1.5688 |
| 87 | $CHCl_2$ | $p\text{-}Cl\text{—}C_6H_4$ | H | H | H | H | H | O | O | 1.5668 |
| 88 | $CH_2BrCHBr$ | $p\text{-}Cl\text{—}C_6H_4$ | H | H | H | H | H | O | O | 1.5814 |
| 89 | $CCl_2=CCl$ | $p\text{-}Cl\text{—}C_6H_4$ | H | H | H | H | H | O | O | 1.5754 |
| 90 | $CCl_2=CCl$ | $m\text{-}ClC_6H_4$ | H | H | H | H | H | S | O | 1.6008 |
| 91 | $CHCl_2$ | $C_6H_5$ | H | H | H | $C_6H_5$ | H | S | O | 1.5653 |
| 92 | $CH_2BrCHBr$ | $C_6H_5$ | H | H | H | $C_6H_5$ | H | S | O | 1.5734 |
| 93 | $CH_2Cl$ | $C_6H_5$ | H | H | H | $C_6H_5$ | H | S | O | 1.5723 |
| 94 | $CHCl_2$ | $3,4\text{-di-}ClC_6H_4$ | H | H | H | H | H | S | O | 1.5600 |
| 95 | $Cl_2CH$ | $p\text{-}\phi\text{-}OCH_3$ | H | H | H | H | H | S | O | 1.5740 |
| 96 | $Cl_2CH$ | $o\text{-}Cl\text{—}\phi$ | H | H | H | H | H | S | O | 97–102° C. |
| 97 | $Cl_2CH$ | $m\text{-}F\text{—}\phi$ | H | H | H | H | H | S | O | 1.5650 |
| 98 | $Cl_2CH$ | $CH_3$ | $CH_3$ | $CH_2OH$ | H | $\phi$ | H | O | O | 1.5190 |
| 99 | $Cl_2CH$ | $CH_3$ | $CH_3$ | $CH_2OCNHCH_3$ (O) | H | $\phi$ | H | O | O | 1.5070 |
| 100 | $Cl_2CH$ | $CH_3$ | $CH_3$ | $CH_2OCCHCl_2$ | H | $\phi$ | H | O | O | 1.5180 |
| 101 | $CH_2Cl$ | $CH_3$ | $CH_3$ | $CH_2OH$ | H | $\phi$ | H | O | O | 1.5182 |
| 102 | $CHCl_2$ | $m\text{-}Cl\phi$ | H | $CH_3$ | H | $CH_3$ | H | O | O | 1.5243 |
| 103 | $CH_2BrCHBr$ | $m\text{-}Cl\phi$ | H | $CH_3$ | H | $CH_3$ | H | O | O | 1.5406 |

Other examples of compounds falling within the generic formula presented herein, which are preparable by the aforedescribed procedures and which may be formulated into herbicidal compositions and applied as herein illustrated, are:

| R | $R_1$ | $R_2$ | $R_3$ | $R_4$ | $R_5$ | $R_6$ | X | Y |
|---|---|---|---|---|---|---|---|---|
| $CH_2Cl$ | $C_6H_5$ | H | H | H | H | H | O | S |
| $CHCl_2$ | $C_6H_5$ | H | H | H | H | H | O | S |
| $CCl_3$ | $C_6H_5$ | H | H | H | H | H | O | S |
| $CH_2Cl$ | $C_6H_5$ | H | H | H | H | H | S | S |
| $CHCl_2$ | $C_6H_5$ | H | H | H | H | H | S | S |
| $CCl_3$ | $C_6H_5$ | H | H | H | H | H | S | S |
| $CH_2Cl$ | $CH_3$ | $CH_3$ | H | H | $C_6H_5$ | H | O | S |
| $CHCl_2$ | $CH_3$ | $CH_3$ | H | H | $C_6H_5$ | H | O | S |
| $CCl_3$ | $CH_3$ | $CH_3$ | H | H | $C_6H_5$ | H | O | S |
| $CH_2Cl$ | $CH_3$ | $CH_3$ | H | H | $C_6H_5$ | H | S | S |
| $CHCl_2$ | $CH_3$ | $CH_3$ | H | H | $C_6H_5$ | H | S | S |
| $CCl_3$ | $CH_3$ | $CH_3$ | H | H | $C_6H_5$ | H | S | S |
| $CH_2BrCHBr$ | $m\text{-}Cl\text{—}C_6H_4$ | H | H | H | $CH_3$ | H | O | S |
| $CH_2BrCHBr$ | $C_6H_5$ | H | H | H | $CH_3$ | H | S | S |
| $CH_2BrCHBr$ | $CH_3$ | $CH_3$ | H | H | $C_6H_5$ | H | O | S |
| $CH_2BrCHBr$ | $CH_3$ | $CH_3$ | H | H | $C_6H_5$ | H | S | S |

The herbicides indicated in the tables and elsewhere are used at rates which produce effective control of undesirable vegetation. The range of rates employed herein produce representative results within the recommended amounts set forth by the supplier. Therefore, the weed control in each instance is commercially acceptable within the desired or recommended amount.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention are prevention of injury to a desired crop species in the presence of a specific compound or combination may be achieved. The beneficial plant species which can be protected by this method is not intended to be limited by the specific crops employed in the examples. The herbicidal compounds employed in the utility of this invention are active herbicides of a general type. That is, the members of the classes are herbicidally effective against a wide range of plant species with no discrimination between desirable and undesirable species. The method of controlling vegetation comprises applying an herbicidally effective amount of the herein described herbicidal compounds to the area or plant locus where control is desired. The compositions as set forth in this invention include those wherein the preferred active herbicidal compound is selected from EPTC, S-ethyl diisobutyl thiocarbamate, S-propyl dipropyl thiocarbamate, S-2,3,3-trichloroallyl-diisopropyl thiocarbamate, S-ethyl cyclohexyl ethyl thiocarbamate, 2-chloro-2',6'-diethyl-N-(methoxymethyl) acetanilide, S-ethyl hexahydro-1H-azepine-1-carbothioate, 2-chloro-N-isopropylacetanilide, N,N-diallyl-2-chloroacetamide, S-4-chlorobenzyl diethyl thiocarbamate, 2-chloro-4-ethylamino-6-isopropylamino-s-triazine, 2-chloro-4,6-bis(ethylamino)-3-triazine, 2(4-chloro-6-ethylamine-s-triazine-2-yl-amino)-2-methylpropionitrile, 2-chloro-4-cyclopropylamino-6-isopropylamino-s-triazine, 2,4-dichlorophenoxyacetic acid, its esters and salts, and 3-(3,4-dichlorophenyl)-1,1-dimethylurea and combinations thereof.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants", it is meant germinant seeds, emerging seedlings and established vegetation including the roots and above-ground portions.

Evaluation Procedures

Flats to be used for growing the crops and weed species were filled with loamy sand soil. Stock solutions of herbicides and antidotes were prepared as follows:

A. Herbicide-2-chloro-2',6'-diethyl-N-(methoxymethyl) acetanilide-LASSO 4E-6.25 g. of LASSO 4E was diluted in 1000 ml. of water. 100 ml. of this solution was applied using a linear spray table, such that the equivalent of 2 lb/A of LASSO was applied in 80 gal. of water per acre to each flat.

B. Antidote-of each candidate 95 mg. was dissolved in 15 ml. of acetone with 1% Tween 20 ® (polyoxyethylene sorbitan monolaurate) so that 1½ml. equals 5 lb/A per flat (based on ½ surface area of a flat).

PES and PPI Tank Mixes

In-furrow application of the antidote employed the above stock solutions (A and B). As a preparatory step, a one pint sample of soil was removed from each flat to be retained and used later to cover the seeds after treatment with the additives. The soil was leveled before planting.

Rows one-quarter inch deep were made lengthweise in each treated flat, preparatory to seeding. After seeding, the flats were sectioned into two equal portions using a wooden barrier and one and one-half ml. of additive stock solution (B) was atomized directly onto the exposed seed and into the furrow in one-half of the flat. The untreated section of the flat served as an herbicide check and also made it possible to observe any lateral movement of the antidote through the soil. The seeds were covered with the one pint sample of untreated soil which had been removed earlier.

The herbicide was applied initially on an individual flat basis by spraying on the soil on a linear spray table the required amount of the herbicide stock solution onto the soil, after seeding and antidote treatment of the furrow.

For tank mixes to be applied as pre-emergence surface application or as pre-plant incorporation, application of the following solutions were used. For 2-chloro-2',6'-diethyl-N-methoxymethyl) acetanilide at 2 lb/A 800 mg. 4E was diluted to 200 ml. with deionized water. To prepare a combined tank mix, 4 ml. of the acetanilide stock solution and 3 ml. of the antidote stock solution (B) were mixed. For the pre-plant incorporation, the same mixed stock solution was injected into the soil during incorporation in a 5 gallon rotary mixer. For pre-emergence surface application, the same stock solution was applied to soil surface after seeding.

The flats were placed on greenhouse benches where temperatures were maintained between 70°-90° F. The soil was watered by sprinkling to assure good plant growth. Injury ratings were taken 2 and 4 weeks after the applications were made. Individual flats treated with the herbicide alone were included to provide a basis for determining the amount of injury reduction provided by the herbicide antidotes.

Some of the candidate antidotes were assayed as antidotes to protect various crops against injury from thiocarbamate herbicides. Selected as representative thiocarbamate herbicides were S-ethyl N,N-dipropylthiocarbamate (EPTC, EPTAM ®) and S-propyl N,N-dipropylthiocarbamate (VERNAM ®). Stock solutions of herbicides and antidotes were prepared and applied in a variety of ways. Soil incorporation, pre-emergence surface application and in-furrow treatment were employed.

Stock solutions for EPTAM ® were prepared as follows:

A. ½lb/A: 670 mg. of EPTC 6E (75.5% a.i.) was diluted with 500 ml. of deionized water so that 2 ml. equals ½lb/A/flat.

B. 5 lb/A: 6700 mg. of EPTC 6E (75.5% a.i.) was diluted with 500 ml. of deionized water so that 2 ml. equals 5 lb/A/flat.

Stock solutions for VERNAM ®:

C. ¾lb/A: 95 mg. of VERNAM° (75% a.i.) was diluted with 100 ml. of deionized water so that 4 ml. applied pre-plant incorporated is equivalent to ¾ lb/A per flat.

D. 1 lb/A: 633 mg. of VERNAM ® (75% a.i.) was diluted with 500 ml. of deionized water so that 4 ml. applied is equivalent to 1 lb/A per flat.

E. 5 lb/A: 633 mg. of VERNAM ® (75 % a.i.) was diluted with 100 ml. of deionized water so that 4 ml. is equivalent to 5 lb/A per flat.

The following table includes results as percent protection of various crops according to the various procedures discussed above. The percent protection is determined by a comparison with flats not treated with the candidate antidotes of this invention.

Treated flats were seeded with DeKalb XL-44 corn (*Zea maize*), sugarbeets (*Beta vulgare*), small seeded

TABLE II

| Application Method: | In-Furrow - IF |
| --- | --- |
| | Pre-Plant Incorporation - PPI (Tank Mix) |
| | Pre-Emergence Surface Application - PES (Tank Mix) |
| Crop Species: | Milo - (*Sorghum vulgare*) |
| Weed Species: | Shatter cane - SC (*Sorghum bicolor*) |
| | Foxtail - ft (*Sataria viridis*) |
| | Crabgrass - CG (*Digitaria sanguinalis*) |
| | Watergrass - WG (*Echinochloa crusgalli*) |

| COMPOUND NUMBER | 5 lb/A - IF | | PPI (5 lb/A) (Tank Mix) | | | | PES (5 lb/A) (Tank Mix) | | | |
| --- | --- | --- | --- | --- | --- | --- | --- | --- | --- | --- |
| | Milo | SC | Milo | Ft | CG | WG | Milo | Ft | CG | WG |
| LASSO 2 lb/A | 100* | 100* | 50 | 100 | 100 | 100 | 70 | 100 | 100 | 100 |
| 1** | 70 | 0 | 0 | 0 | 0 | 0 | 0 | 0 | 0 | 0 |
| 2 | 20 | 0 | 0 | 0 | 0 | 0 | 0 | 0 | 0 | 0 |
| 3 | 50 | 0 | 0 | 0 | 0 | 0 | 0 | 0 | 0 | 0 |
| 4 | 60 | 50 | 100 | 0 | 0 | 0 | 70 | 0 | 0 | 0 |
| 6 | 20 | 0 | 0 | 0 | 0 | 0 | 0 | 0 | 0 | 0 |
| 10 | 0 | 0 | 80 | 0 | 0 | 0 | 14 | 0 | 0 | 0 |
| 11 | 60 | 0 | 60 | 0 | 0 | 0 | 0 | 0 | 0 | 0 |
| 14 | 0 | 0 | 40 | 0 | 0 | 0 | 0 | 0 | 0 | 0 |
| 15 | 15 | 0 | 60 | 0 | 0 | 0 | 14 | 0 | 0 | 0 |
| 18 | 0 | 0 | 40 | 0 | 0 | 0 | 14 | 0 | 0 | 0 |
| 20 | 80 | 90 | 100 | 0 | 20 | 10 | 85 | 0 | 0 | 0 |
| 21 | 15 | 0 | 0 | 0 | 0 | 0 | 0 | 0 | 0 | 0 |
| 22 | 90 | 90 | 100 | 0 | 0 | 0 | 100 | 0 | 0 | 0 |
| 23 | 70 | 70 | 0 | 0 | 0 | 0 | 0 | 0 | 0 | 0 |
| 24 | 15 | 0 | 40 | 0 | 0 | 0 | 28 | 0 | 0 | 0 |
| 27 | 0 | 0 | 40 | 0 | 0 | 0 | 0 | 0 | 0 | 0 |
| 29 | 0 | 0 | 40 | 0 | 0 | 0 | 0 | 0 | 0 | 0 |
| 32 | 0 | 0 | 40 | 0 | 0 | 0 | 14 | 0 | 0 | 0 |
| 35 | 30 | 0 | 0 | 0 | 0 | 0 | 0 | 0 | 0 | 0 |
| 42 | 50 | 0 | 20 | 0 | 0 | 0 | 0 | 0 | 0 | 0 |
| 43 | 60 | 0 | 0 | 0 | 0 | 0 | 0 | 0 | 0 | 0 |
| 46 | 25 | 0 | 40 | 0 | 0 | 0 | 14 | 0 | 0 | 0 |
| 47 | 50 | 0 | 0 | 0 | 0 | 0 | 0 | 0 | 0 | 0 |
| 48 | 30 | 0 | 0 | 0 | 0 | 0 | 0 | 0 | 0 | 0 |
| 49 | 40 | 0 | 0 | 0 | 0 | 0 | 0 | 0 | 0 | 0 |
| 50 | 50 | 0 | 40 | 0 | 0 | 0 | 0 | 0 | 0 | 0 |
| 51 | 30 | 0 | 0 | 0 | 0 | 0 | 0 | 0 | 0 | 0 |
| 52 | 0 | 0 | 40 | 0 | 0 | 0 | 28 | 0 | 0 | 0 |
| 53 | 50 | 0 | 0 | 0 | 0 | 0 | 0 | 0 | 0 | 0 |
| 54 | 20 | 0 | 0 | 0 | 0 | 0 | 0 | 0 | 0 | 0 |
| 55 | 60 | 0 | 20 | 0 | 0 | 0 | 28 | 0 | 0 | 0 |
| 56 | 20 | 0 | 20 | 0 | 0 | 0 | 0 | 0 | 0 | 0 |
| 57 | 30 | 0 | 0 | 0 | 0 | 0 | 0 | 0 | 0 | 0 |
| 58 | 60 | 0 | 0 | 0 | 0 | 0 | 0 | 0 | 0 | 0 |
| 59 | 30 | 0 | 80 | 0 | 30 | 0 | 0 | 0 | 0 | 0 |
| 63 | 20 | 0 | 80 | 0 | 0 | 0 | 14 | 0 | 0 | 0 |
| 64 | 50 | 0 | 0 | 0 | 0 | 0 | 0 | 0 | 0 | 0 |
| 65 | 30 | 0 | 0 | 0 | 0 | 0 | 0 | 0 | 0 | 0 |
| 67 | 0 | 0 | 40 | 0 | 0 | 0 | 28 | 0 | 0 | 0 |
| 68 | 80 | 0 | 0 | 0 | 0 | 0 | 0 | 0 | 0 | 0 |
| 70 | 40 | 0 | 0 | 0 | 0 | 0 | 0 | 0 | 0 | 0 |
| 72 | 50 | 0 | 0 | 0 | 0 | 0 | 0 | 0 | 0 | 0 |
| 73 | 15 | 0 | 60 | 0 | 0 | 0 | 0 | 0 | 0 | 0 |
| 75 | 40 | 0 | 80 | 0 | 0 | 0 | 65 | 0 | 0 | 0 |
| 76 | 40 | 0 | 0 | 0 | 0 | 0 | 0 | 0 | 0 | 0 |
| 77 | 40 | 0 | 0 | 0 | 0 | 0 | 0 | 0 | 0 | 0 |
| 78 | 5 | — | 16 | 0 | 0 | 0 | 20 | 0 | 0 | 0 |
| 79 | 80 | — | 50 | 0 | 0 | 0 | 50 | 0 | 0 | 0 |
| 80 | 20 | — | 0 | 0 | 0 | 0 | 16 | 0 | 0 | 0 |
| 81 | 15 | — | 0 | 0 | 0 | 0 | 0 | 0 | 0 | 0 |
| 83 | 15 | — | 0 | 0 | 0 | 0 | 16 | 0 | 0 | 0 |
| 84 | 60 | — | 50 | 0 | 0 | 0 | 50 | 0 | 0 | 0 |
| 85 | 0 | — | 20 | 0 | 0 | 0 | 50 | 0 | 0 | 0 |
| 87 | 50 | — | 40 | 0 | 0 | 0 | 67 | 0 | 0 | 0 |
| 88 | 0 | — | 30 | 0 | 0 | 0 | 16 | 0 | 0 | 0 |
| 89 | 30 | — | 30 | 0 | 0 | 0 | 16 | 0 | 0 | 0 |
| 90 | 30 | — | 0 | 0 | 0 | 0 | 0 | 0 | 0 | 0 |
| 91 | 15 | — | 0 | 0 | 0 | 0 | 16 | 0 | 0 | 0 |
| 92 | 40 | — | 0 | 0 | 0 | 0 | 0 | 0 | 0 | 0 |
| 94 | 40 | — | 50 | 0 | 0 | 0 | 40 | 0 | 0 | 0 |

— = not tested.
\* = % injury
\*\* = % protection

Thiocarbamate Herbicide Multicrop Screen gray striped sunflower (*Helianthus annus*), soybeans (Glycine max) and oilseed rape (Brassica napus), milo [sorghum] (sorgum vulgare), wheat (Triticum aestivum), green foxtail (Sataria viridis), rice (Oryza sativa) and barley (Hordeum vulgare). Seeds were then covered with the pint soil sample removed prior to seeding.

The flats were then placed on greenhouse benches where temperatures were maintained between 70°–90° F. The soil was watered by sprinkling to assure good plant growth.

Injury ratings were taken 2 and 4 weeks after the treatments were applied. Soil treated with the herbicide alone at the indicated rate was included to provide a basis for determining the amount of injury reduction provided by the herbicide antidotes. The percent protection of various representative crops is reported in Table III. The percent protection is determined by a comparison with flats not treated with the candidate antidote.

TABLE III
MULTICROP SCREEN RESULTS

| COMPOUND NUMBER | Method of Antidote Application | Herbicide/ Rate lb/A | Crop Protected | Percent Protection |
|---|---|---|---|---|
| 1 | PPI | EPTC/½ | Milo | 30 |
|   |   |   | Rice | 63 |
|   |   |   | Barley | 30 |
| 2 | PPI | EPTC/5 | Corn | 100 (2 wks) |
| 3 | PPI | EPTC/5 | Rice | 63 |
|   |   |   | Corn | 100 |
| 4 | PPI | EPTC/½ | Milo | 50 |
| 6 | PPI | EPTC/½ | Milo | 40 |
| 9 | PPI | EPTC/½ | Rice | 100 |
|   |   |   | Barley | 50 |
| 11 | PPI | EPTC/½ | Milo | 50 |
|   |   |   | Corn | 100 |
| 13 | PPI | EPTC/5 | Sunflower | 67 |
| 15 | PPI | EPTC/½ | Rice | 100 |
|   |   | EPTC/5 | Corn | 65 |
| 16 | PPI | EPTC/½ | Rice | 100 |
|   |   | EPTC/5 | Corn | 65 |
| 17 | PPI | EPTC/½ | Rice | 100 |
| 22 | PPI | EPTC/½ | Milo | 90 |
|   |   | EPTC/5 | Corn | 100 |
| 23 | PPI | EPTC/½ | Milo | 67 |
|   |   | EPTC/½ | Rice | 55 |
|   |   | EPTC/5 | Sunflower | 30 |
| 28 | PPI | EPTC/5 | Sunflower | 67 |
| 31 | PPI | EPTC/5 | Sugarbeet | 70 |
| 33 | PPI | EPTC/½ | Rice | 44 |
|   |   | EPTC/½ | Barley | 40 |
| 34 | PPI | EPTC/½ | Milo | 10 |
| 35 | PPI | EPTC/½ | Milo | 45 |
| 36 | PPI | EPTC/5 | Sugarbeet | 80 |
| 38 | PPI | EPTC/5 | Corn | 33 |
| 39 | PPI | EPTC/½ | Barley | 40 |
|   |   | EPTC/5 | Corn | 55 |
| 40 | PPI | EPTC/5 | Corn | 22 |
| 41 | PPI | EPTC/5 | Sunflower | 67 |
| 42 | PPI | EPTC/5 | Corn | 22 |
| 47 | PPI | EPTC/½ | Milo | 75 |
|   |   |   | Wheat | 67 |
|   |   |   | Rice | 78 |
|   |   |   | Barley | 63 |
|   |   | EPTC/5 | Corn | 100 |
| 48 | PPI | EPTC/½ | Milo | 25 |
| 51 | PPI | EPTC/½ | Barley | 67 |
| 53 | PPI | EPTC/½ | Barley | 50 |
|   |   | EPTC/5 | Corn | 100 |
| 54 | PPI | EPTC/5 | Corn | 40 |
| 57 | PPI | EPTC/5 | Oilseed rape | 67 |
| 60 | PPI | EPTC/5 | Corn | 100 |
| 65 | PPI | EPTC/5 | Corn | 50 |
| 67 | PPI | EPTC/½ | Rice | 100 |
| 68 | PPI | EPTC/½ | Rice | 100 |
| 70 | PPI | EPTC/½ | Wheat | 78 |
|   |   |   | Barley | 85 |
|   |   |   | Rice | 100 |
| 72 | PPI | EPTC/½ | Rice | 85 |

TABLE III-continued
MULTICROP SCREEN RESULTS

| COMPOUND NUMBER | Method of Antidote Application | Herbicide/ Rate lb/A | Crop Protected | Percent Protection |
|---|---|---|---|---|
|   |   | EPTC/½ | Barley | 85 |
| 73 | PPI | EPTC/½ | Barley | 50 |
| 75 | PPI | EPTC/½ | Rice | 85 |
|   |   |   | Barley | 72 |
|   |   | EPTC/5 | Corn | 50 |
| 76 | IF/5 lb/A | EPTC/5 | Corn | 100 |
| 77 | IF/5 lb/A | EPTC/5 | Corn | 50 |
| VERNAM/ |   | VERNAM/5 | Corn | 60* Injury |
| 6E |   |   | Milo | 100 |
|   |   |   | Wheat | 98 |
|   |   |   | Barley | 90 |
| 2 | IF/5 lb/A | VERNAM/5 | Corn | 50 |
| 3 | IF/5 lb/A | VERNAM/5 | Corn | 50 |
| 4 | IF/5 lb/A | VERNAM/5 | Corn | 100 |
| 11 | IF/5 lb/A | VERNAM/5 | Corn | 100 |
|   |   | VERNAM/¾ | Milo | 50 |
| 18 | IF/5 lb/A | VERNAM/5 | Corn | 100 |
| 20 | IF/5 lb/A | VERNAM/5 | Corn | 100 |
|   |   | VERNAM/¾ | Milo | 60 |
| 22 | IF/5 lb/A | VERNAM/5 | Corn | 100 |
|   |   | VERNAM/¾ | Milo | 90 |
| 23 | IF/5 lb/A | VERNAM/5 | Corn | 100 |
| 24 | IF/5 lb/A | VERNAM/5 | Corn | 84 |
|   |   | VERNAM/¾ | Milo | 40 |
| 26 | IF/5 lb/A | VERNAM/¾ | Barley | 67 |
| 35 | IF/5 lb/A | VERNAM/¾ | Corn | 67 |
|   |   | VERNAM/¾ | Milo | 40 |
| 38 | IF/5 lb/A | VERNAM/5 | Corn | 50 |
| 39 | IF/5 lb/A | VERNAM/5 | Corn | 100 |
|   |   | VERNAM/¾ | Barley | 55 |
| 40 | IF/5 lb/A | VERNAM/5 | Corn | 67 |
| 47 | IF/5 lb/A | VERNAM/5 | Corn | 100 |
|   |   | VERNAM/¾ | Milo | 50 |
| 53 | IF/5 lb/A | VERNAM/5 | Corn | 100 |
| 60 | IF/5 lb/A | VERNAM/5 | Corn | 100 |
| 78 | IF/5 lb/A | VERNAM/1 | Milo | 50 |
|   |   | VERNAM/5 | Corn | 22 |
| 79 | IF/5 lb/A | VERNAM/1 | Milo | 60 |
|   |   | VERNAM/5 | Corn | 88 |
| 80 | IF/5 lb/A | VERNAM/1 | Milo | 30 |
|   |   | VERNAM/5 | Corn | 88 |
| 81 | IF/5 lb/A | VERNAM/5 | Corn | 20 |
| 82 | IF/5 lb/A | VERNAM/5 | Corn | 45 (2 wks) |

TABLE III-continued
MULTICROP SCREEN RESULTS

| Compound Number | Method of Antidote Application | Herbicide/ Rate lb/A | Crop Protected | Percent Protection |
|---|---|---|---|---|
| 83 | IF/5 lb/A | VERNAM/1 | Barley | 50 |
| 84 | IF/5 lb/A | VERNAM/1 | Milo | 40 |
|  |  | VERNAM/5 | Corn | 88 |
| 85 | IF/5 lb/A | VERNAM/1 | Wheat | 40 |
|  |  | VERNAM/1 | Barley | 45 |
|  |  | VERNAM/5 | Corn | 67 |
| 86 | IF/5 lb/A | VERNAM/1 | Barley | 55 |
|  |  | VERNAM/5 | Corn | 78 |
| 87 | IF/5 lb/A | VERNAM/1 | Milo | 50 |
|  |  | VERNAM/1 | Barley | 45 |
|  |  | VERNAM/5 | Corn | 67 |
| 88 | IF/5 lb/A | VERNAM/1 | Barley | 55 |
| 90 | IF/5 lb/A | VERNAM/1 | Barley | 33 |
|  |  | VERNAM/5 | Soybeans | 30 |
| 91 | IF/5 lb/A | VERNAM/5 | Corn | 36 |
| 94 | IF/5 lb/A | VERNAM/5 | Corn | 23 |
| 95 | IF/5 lb/A | VERNAM/1 | Wheat | 44 |
|  |  | VERNAM/1 | Barley | 44 |
|  |  | VERNAM/5 | Corn | 100 |
| 96 | IF/5 lb/A | VERNAM/1 | Wheat | 67 |
|  |  | VERNAM/1 | Barley | 44 |
|  |  | VERNAM/5 | Corn | 37.5 |
| 97 | IF/5 lb/A | VERNAM/5 | Corn | 87.5 |
| 98 | IF/5 lb/A | VERNAM/5 | Corn | 37.5 |
| 99 | IF/5 lb/A | VERNAM/5 | Corn | 75 |
| 100 | IF/5 lb/A | VERNAM/1 | Milo | 20 |
|  |  | VERNAM/1 | Barley | 22 |
| 101 | IF/5 lb/A | VERNAM/1 | Milo | 20 |
|  |  | VERNAM/1 | Barley | 44 |
| 102 | IF/5 lb/A | VERNAM/6** | Corn | 100 |
| 103 | IF/5 lb/A | VERNAM/1 | Wheat | 33 |
|  |  | VERNAM/1 | Barley | 33 |

**Stock solution for VERNAM 6E at 6 lb/A PPI (pre-plant incorporated) 3800 mg/500 ml. water; such that 4 ml. = 6 lb/A PPI The compounds and compositions of this invention were employed in effective herbicidal compositions comprising the antidote and a representative thiocarbamate herbicide and the antidote and a representative helogenated acetanilide herbicide, as described hereinabove. The herbicidal compositions were tested in the following manner.

The compositions of the present invention for the protection of cultivated crop plants comprise an active herbicidal compound and an antidote therefor selected from the abovedescribed compounds. The compositions of herbicide and antidote can be prepared by conventional methods through the thorough mixing and grinding of the active herbicide agents and the antidote with suitable carriers and/or other distribution media, possibly with the addition of dispersion agents or solvents.

The antidote compounds and compositions of the present invention can be used in any convenient form. Thus, the antidote compounds can be formulated into emulsifiable liquids, emulsifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not affect the herbicidal activity of the herbicides.

The amount of antidote compound present can range between about 0.0001 to about 30 parts by weight of antidote compound described herein per each part by weight of herbicide. The exact amount of antidote compound will usually be determined on economic ratios for the most effective amount usable. It is understood that a non-phytotoxic quantity of antidote compound will be employed in the herbicidal compositions described herein.

What is claimed is:

1. The method of protecting a crop from injury, said injury due to a substituted acetanilide herbicide, comprising pre-plant incorporation in the soil in which said crop is to be planted and grown, a non-phytotoxic antidotally effective amount of a compound corresponding to the formula

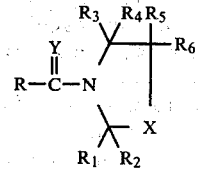

in which X and Y are independently oxygen or sulfur; R is haloalkyl having 1 to 6 carbon atoms, inclusive, or chloroalkenyl having 2 to 4 carbon atoms, inclusive; $R_1$ is hydrogen, lower alkyl having 1 to 4 carbon atoms, inclusive, phenyl, naphthyl, substituted phenyl wherein said substituents are mono-fluoro, mono- or di-chloro, nitro, methyl, methoxy, or hydroxyl; $R_2$ is hydrogen or lower alkyl having 1 to 4 carbon atoms, inclusive; $R_3$ is hydrogen, lower alkyl having 1 to 4 carbon atoms, inclusive, hydroxymethyl, N-methylcarbamoyloxymethyl or dichloroacetoxymethyl; $R_4$ is hydrogen, or loeer alkyl having 1 to 4 carbon atoms, inclusive; $R_5$ is hydrogen, lower alkyl having 1 to 4 carbon atoms, inclusive, or phenyl; and $R_6$ is hydrogen; provided that at least one of $R_1$ or $R_5$ is phenyl, substituted phenyl or naphthyl; said compound being antidotally active with said acetanilide herbicide compound and wherein said compound is present in an amount between about 0.0001 to about 30 parts by weight of antidote compound per each part by weight of herbicide.

2. The method according to claim 1 in which X is oxygen, Y is oxygen, R is haloalkyl, $R_1$ is nitrophenyl, $R_2$, $R_3$, $R_4$, $R_5$ and $R_6$ are each hydrogen.

3. The method according to claim 2 in which R is dichloromethyl and $R_1$ is meta-nitrophenyl.

4. The method according to claim 1 in which X is oxygen, Y is oxygen, R is haloalkyl, $R_1$ is phenyl and $R_2$, $R_3$, $R_4$, $R_5$ and $R_6$ are each hydrogen.

5. The method according to claim 4 in which R is dichloromethyl.

6. The method according to claim 4 in which R is trichloromethyl.

7. The method according to claim 4 in which R is 1-bromoethyl.

8. The method according to claim 4 in which R is 1,1-dichloroethyl.

9. The method according to claim 4 in which R is dibromomethyl.

10. The method according to claim 4 in which R is 1,2-dibromoethyl.

11. The method according to claim 1 in which X is oxygen, Y is oxygen, R is haloalkyl, $R_1$ is chlorophenyl and $R_2$, $R_3$, $R_4$, $R_5$ and $R_6$ are each hydrogen.

12. The method according to claim 11 in which R is dichloromethyl and $R_1$ is meta-chlorophenyl.

13. The method according to claim 11 in which R is trichloromethyl and $R_1$ is meta-chlorophenyl.

14. The method according to claim 11 in which R is monochloromethyl and $R_1$ is meta-chlorophenyl.

15. The method according to claim 11 in which R is monobromomethyl and $R_1$ is meta-chlorophenyl.

16. The method according to claim 11 in which R is 1-bromoethyl and $R_1$ is meta-chlorophenyl.

17. The method according to claim 11 in which R is dibromomethyl and $R_1$ is meta-chlorophenyl.

18. The method according to claim 11 in which R is 1,2-dibromoethyl and $R_1$ is meta-chlorophenyl.

19. The method according to claim 1 in which X is oxygen, Y is oxygen, R is haloalkyl, $R_1$ is lower alkyl, $R_2$, $R_3$, $R_4$ and $R_6$ are each hydrogen and $R_5$ is phenyl.

20. The method according to claim 19 in which R is dichloromethyl and $R_1$ is ethyl.

21. The method according to claim 19 in which R is trichloromethyl and $R_1$ is ethyl.

22. The method according to claim 1 in which X is oxygen, Y is oxygen, R is haloalkyl, $R_1$ is lower alkyl, $R_2$ is lower alkyl, $R_3$, $R_4$ and $R_6$ are each hydrogen and $R_5$ is phenyl.

23. The method according to claim 22 in which R is dichloromethyl, $R_1$ is methyl and $R_2$ is methyl.

24. The method according to claim 22 in which R is dichloromethyl, $R_1$ is methyl and $R_2$ is methyl.

25. The method according to claim 1 in which X is oxygen, Y is oxygen, R is haloalkyl, $R_1$ is phenyl, $R_2$ and $R_6$ are each hydrogen, $R_3$, $R_4$ and $R_5$ are each lower alkyl.

26. The method according to claim 25 in which R is monochloromethyl and $R_3$, $R_4$ and $R_5$ are each methyl.

27. The method according to claim 25 in which R is dichloromethyl and $R_3$, $R_4$ and $R_5$ are each methyl.

28. The method according to claim 25 in which R is trichloromethyl and $R_3$, $R_4$ and $R_5$ are each methyl.

29. The method according to claim 25 in which R is 1,1-dichloroethyl and $R_3$, $R_4$ and $R_5$ are each methyl.

30. The method according to claim 1 in which X is sulfur, Y is oxygen, R is haloalkyl, $R_1$ is phenyl, $R_2$, $R_3$, $R_4$, $R_5$ and $R_6$ are each hydrogen.

31. The method according to claim 30 in which R is monochloromethyl.

32. The method according to claim 30 in which R is dichloromethyl.

33. The method according to claim 30 in which R is trichloromethyl.

34. The method according to claim 30 in which R is 1,1-dichloroethyl.

35. The method according to claim 30 in which R is 2-bromoethyl.

36. The method according to claim 30 in which R is 1,2-dibromoethyl.

37. The method according to claim 1 in which X is sulfur, Y is oxygen, R is haloalkyl, $R_1$ is chlorophenyl and $R_2$, $R_3$, $R_4$, $R_5$ and $R_6$ are each hydrogen.

38. The method according to claim 37 in which R is monochloromethyl and $R_1$ is meta-chlorophenyl.

39. The method according to claim 37 in which R is dichloromethyl and $R_1$ is meta-chlorophenyl.

40. The method according to claim 37 in which R is trichloromethyl and $R_1$ is meta-chlorophenyl.

41. The method according to claim 37 in which R is 1,1-dichloroethyl and $R_1$ is meta-chlorophenyl.

42. The method according to claim 37 in which R is 2-bromoethyl and $R_1$ is meta-chlorophenyl.

43. The method according to claim 37 in which R is 1,2-dibromoethyl and $R_1$ is meta-chlorophenyl.

44. The method according to claim 37 in which R is 2-chloroethyl and $R_1$ is meta-chlorophenyl.

45. The method according to claim 1 in which X is sulfur, Y is oxygen, R is haloalkyl, $R_1$ is chlorophenyl and $R_2$, $R_3$, $R_4$, $R_5$ and $R_6$ are each hydrogen.

46. The method according to claim 1 in which X is oxygen, Y is oxygen, R is haloalkyl, $R_5$ is phenyl and $R_2$, $R_3$, $R_4$ and $R_6$ are each hydrogen.

47. The method according to claim 46 in which R is 2-bromoethyl.

* * * * *